US012070929B2

(12) United States Patent
Hjelmgaard

(10) Patent No.: US 12,070,929 B2
(45) Date of Patent: Aug. 27, 2024

(54) MINERAL WOOL PRODUCT

(71) Applicant: ROCKWOOL INTERNATIONAL A/S, Hedehusene (DK)

(72) Inventor: Thomas Hjelmgaard, Fredensborg (DK)

(73) Assignee: ROCKWOOL A/S, Hedehusene (DK)

( * ) Notice: Subject to any disclaimer, the term of this patent is extended or adjusted under 35 U.S.C. 154(b) by 1160 days.

(21) Appl. No.: 16/099,317

(22) PCT Filed: May 11, 2017

(86) PCT No.: PCT/EP2017/061417
§ 371 (c)(1),
(2) Date: Nov. 6, 2018

(87) PCT Pub. No.: WO2017/194723
PCT Pub. Date: Nov. 16, 2017

(65) Prior Publication Data
US 2019/0136427 A1    May 9, 2019

(30) Foreign Application Priority Data

May 13, 2016   (EP) .................................... 16169635
May 13, 2016   (EP) .................................... 16169638
May 13, 2016   (EP) .................................... 16169641

(51) Int. Cl.
*B32B 37/12*     (2006.01)
*B32B 5/12*      (2006.01)
(Continued)

(52) U.S. Cl.
CPC ................ *B32B 37/12* (2013.01); *B32B 5/12* (2013.01); *B32B 5/26* (2013.01); *B32B 7/12* (2013.01);
(Continued)

(58) Field of Classification Search
None
See application file for complete search history.

(56) References Cited

U.S. PATENT DOCUMENTS 3,411,972 A    11/1968   Salyer
3,824,086 A     7/1974   Perry
(Continued)

FOREIGN PATENT DOCUMENTS

CN     101302410 A    11/2008
CN     102068008 A     5/2011
(Continued)

OTHER PUBLICATIONS

Ma, Wen et al., "Characterization of gelatin-based edible films incorporated with olive oil", Food Research International, 49 (2012), pp. 572-579.
(Continued)

*Primary Examiner* — Christopher T Schatz
(74) *Attorney, Agent, or Firm* — Abel Schillinger, LLP

(57) ABSTRACT

The invention relates to a method of bonding together surfaces of two or more elements, whereby at least one of the two or more elements is a mineral wool element, said mineral wool element(s) being bound by a mineral wool binder, the method comprising the steps of providing two or more elements; applying an adhesive to one or more of the surfaces to be bonded together before, during or after contacting the surfaces to be bonded together with each other; curing the adhesive, wherein the adhesive comprises at least one protein; at least one phenol and/or quinone containing compound, and/or at least one enzyme.

18 Claims, 1 Drawing Sheet

(51) Int. Cl.

| | | |
|---|---|---|
| B32B 5/26 | (2006.01) | |
| B32B 7/12 | (2006.01) | |
| B32B 15/14 | (2006.01) | |
| B32B 19/04 | (2006.01) | |
| B32B 37/14 | (2006.01) | |
| B32B 37/18 | (2006.01) | |
| B32B 38/00 | (2006.01) | |
| C03C 13/06 | (2006.01) | |
| C03C 25/26 | (2018.01) | |
| C03C 25/32 | (2018.01) | |
| C03C 25/321 | (2018.01) | |
| C03C 25/328 | (2018.01) | |
| C08J 5/04 | (2006.01) | |
| C08L 1/28 | (2006.01) | |
| C08L 3/02 | (2006.01) | |
| C08L 5/12 | (2006.01) | |
| C08L 89/06 | (2006.01) | |
| C09J 5/00 | (2006.01) | |
| C09J 11/06 | (2006.01) | |
| C09J 101/28 | (2006.01) | |
| C09J 103/02 | (2006.01) | |
| C09J 105/00 | (2006.01) | |
| C09J 105/04 | (2006.01) | |
| C09J 105/06 | (2006.01) | |
| C09J 105/12 | (2006.01) | |
| C09J 189/00 | (2006.01) | |
| C09J 189/06 | (2006.01) | |
| D04H 1/413 | (2012.01) | |
| D04H 1/4209 | (2012.01) | |
| D04H 1/4218 | (2012.01) | |
| D04H 1/4266 | (2012.01) | |
| D04H 1/587 | (2012.01) | |
| D04H 1/593 | (2012.01) | |
| D04H 1/64 | (2012.01) | |
| D04H 1/724 | (2012.01) | |
| D04H 1/74 | (2006.01) | |
| D04H 3/002 | (2012.01) | |
| D04H 3/004 | (2012.01) | |
| E04B 1/74 | (2006.01) | |
| E04B 1/80 | (2006.01) | |
| E04B 1/88 | (2006.01) | |
| E04B 1/94 | (2006.01) | |
| E04C 2/284 | (2006.01) | |
| E04D 3/35 | (2006.01) | |
| E04F 13/08 | (2006.01) | |
| C12N 9/02 | (2006.01) | |
| C12N 9/06 | (2006.01) | |
| C12N 9/08 | (2006.01) | |
| C12N 9/10 | (2006.01) | |
| C12N 9/90 | (2006.01) | |
| E04B 1/76 | (2006.01) | |

(52) U.S. Cl.
CPC .............. *B32B 15/14* (2013.01); *B32B 19/04* (2013.01); *B32B 19/041* (2013.01); *B32B 37/1207* (2013.01); *B32B 37/146* (2013.01); *B32B 37/18* (2013.01); *B32B 38/0004* (2013.01); *C03C 13/06* (2013.01); *C03C 25/26* (2013.01); *C03C 25/32* (2013.01); *C03C 25/321* (2013.01); *C03C 25/328* (2013.01); *C08J 5/043* (2013.01); *C08L 1/286* (2013.01); *C08L 3/02* (2013.01); *C08L 5/12* (2013.01); *C08L 89/06* (2013.01); *C09H 11/00* (2013.01); *C09J 5/00* (2013.01); *C09J 11/06* (2013.01); *C09J 101/28* (2013.01); *C09J 101/286* (2013.01); *C09J 103/02* (2013.01); *C09J 105/00* (2013.01); *C09J 105/04* (2013.01); *C09J 105/06* (2013.01); *C09J 105/12* (2013.01); *C09J 189/005* (2013.01); *C09J 189/06* (2013.01); *D04H 1/413* (2013.01); *D04H 1/4209* (2013.01); *D04H 1/4218* (2013.01); *D04H 1/4266* (2013.01); *D04H 1/587* (2013.01); *D04H 1/593* (2013.01); *D04H 1/64* (2013.01); *D04H 1/724* (2013.01); *D04H 1/74* (2013.01); *D04H 3/002* (2013.01); *D04H 3/004* (2013.01); *E04B 1/74* (2013.01); *E04B 1/80* (2013.01); *E04B 1/88* (2013.01); *E04B 1/94* (2013.01); *E04C 2/284* (2013.01); *E04D 3/352* (2013.01); *E04F 13/0866* (2013.01); *B32B 2037/1215* (2013.01); *B32B 2037/1253* (2013.01); *B32B 2037/1269* (2013.01); *B32B 38/164* (2013.01); *B32B 2250/20* (2013.01); *B32B 2250/40* (2013.01); *B32B 2255/02* (2013.01); *B32B 2255/26* (2013.01); *B32B 2262/108* (2013.01); *B32B 2305/20* (2013.01); *B32B 2305/72* (2013.01); *B32B 2307/304* (2013.01); *B32B 2307/732* (2013.01); *B32B 2309/02* (2013.01); *B32B 2315/14* (2013.01); *B32B 2317/00* (2013.01); *B32B 2419/06* (2013.01); *B32B 2607/00* (2013.01); *C03C 2213/00* (2013.01); *C03C 2218/11* (2013.01); *C08J 2301/28* (2013.01); *C08J 2303/02* (2013.01); *C08J 2389/06* (2013.01); *C08J 2405/00* (2013.01); *C08J 2405/04* (2013.01); *C08J 2405/06* (2013.01); *C08J 2405/12* (2013.01); *C08J 2491/00* (2013.01); *C08J 2493/00* (2013.01); *C08L 2201/52* (2013.01); *C08L 2205/03* (2013.01); *C09J 2400/146* (2013.01); *C09J 2401/00* (2013.01); *C09J 2403/00* (2013.01); *C09J 2405/00* (2013.01); *C09J 2489/00* (2013.01); *C12N 9/0022* (2013.01); *C12N 9/0051* (2013.01); *C12N 9/0059* (2013.01); *C12N 9/0065* (2013.01); *C12N 9/0071* (2013.01); *C12N 9/1044* (2013.01); *C12N 9/90* (2013.01); *C12Y 104/03013* (2013.01); *C12Y 108/03002* (2013.01); *C12Y 110/03001* (2013.01); *C12Y 111/01007* (2013.01); *C12Y 114/18001* (2013.01); *C12Y 203/01013* (2013.01); *C12Y 203/02013* (2013.01); *C12Y 503/04001* (2013.01); *D10B 2505/20* (2013.01); *E04B 2001/742* (2013.01); *E04B 2001/743* (2013.01); *E04B 2001/745* (2013.01); *E04B 2001/7683* (2013.01)

(56) References Cited

U.S. PATENT DOCUMENTS

| | | |
|---|---|---|
| 4,040,213 A | 8/1977 | Capaul |
| 4,283,457 A | 8/1981 | Kolsky et al. |
| 4,552,793 A | 11/1985 | Cameron et al. |
| 4,613,627 A | 9/1986 | Sherman |
| 5,218,783 A | 6/1993 | Langezaal |
| 5,298,205 A | 3/1994 | Hayes et al. |
| 5,318,990 A | 6/1994 | Strauss |
| 5,430,070 A | 7/1995 | Kono |
| 5,731,183 A | 3/1998 | Kobayshi et al. |
| 2003/0175335 A1 | 9/2003 | Scott |
| 2004/0069770 A1 | 4/2004 | Cary et al. |
| 2004/0192616 A1 | 9/2004 | Kiel et al. |
| 2007/0027283 A1 | 2/2007 | Swift |
| 2007/0036975 A1 | 2/2007 | Miele et al. |

(56) References Cited

U.S. PATENT DOCUMENTS

| | | |
|---|---|---|
| 2007/0142596 A1 | 6/2007 | Swift et al. |
| 2007/0173588 A1 | 7/2007 | Espiard |
| 2008/0003346 A1 | 1/2008 | Boyer |
| 2008/0003902 A1 | 1/2008 | Boyer |
| 2008/0213597 A1 | 9/2008 | Li |
| 2010/0096580 A1 | 4/2010 | Daschkeit |
| 2010/0282996 A1 | 11/2010 | Jaffrennou et al. |
| 2010/0286640 A1 | 11/2010 | Nordby et al. |
| 2010/0297380 A1 | 11/2010 | Szakola et al. |
| 2010/0330376 A1 | 12/2010 | Trksak |
| 2011/0003522 A1 | 1/2011 | Chen |
| 2011/0021101 A1 | 1/2011 | Hawkins |
| 2011/0101260 A1 | 5/2011 | Pons Y Moll et al. |
| 2011/0200814 A1 | 8/2011 | Hernandez-Torres |
| 2011/0223364 A1 | 9/2011 | Hawkins |
| 2011/0266488 A1 | 11/2011 | Didier |
| 2012/0190262 A1 | 7/2012 | Rosenberg et al. |
| 2013/0283688 A1 | 10/2013 | Naerum |
| 2014/0083328 A1 | 3/2014 | Lochel, Jr. |
| 2014/0148532 A1 | 5/2014 | Omura |
| 2015/0373924 A1 | 12/2015 | Janssen |

FOREIGN PATENT DOCUMENTS

| | | |
|---|---|---|
| CN | 102459320 A | 5/2012 |
| CN | 103476300 A | 12/2013 |
| DE | 4130077 A1 | 3/1993 |
| EA | 014260 B1 | 12/2008 |
| EA | 017247 B1 | 2/2010 |
| EA | 019897 B1 | 12/2010 |
| EP | 0058306 A2 | 8/1982 |
| EP | 0498971 A1 | 8/1992 |
| EP | 583086 A | 2/1994 |
| EP | 0708161 A1 | 4/1996 |
| EP | 0726317 A2 | 8/1996 |
| EP | 0741003 A1 | 11/1996 |
| EP | 990727 A1 | 4/2000 |
| EP | 1020198 A2 | 7/2000 |
| EP | 1184033 A1 | 3/2002 |
| EP | 1741726 A1 | 1/2007 |
| EP | 2246312 A2 | 11/2010 |
| EP | 2424886 B1 | 4/2013 |
| EP | 2738232 A1 | 6/2014 |
| EP | 2990494 A1 | 3/2016 |
| ES | 1074717 U | 6/2011 |
| FR | 2307858 A1 | 11/1976 |
| GB | 849833 A | 9/1960 |
| GB | 926749 A | 5/1963 |
| GB | 1215113 A | 12/1970 |
| NL | 1001508 C2 | 5/1997 |
| RU | 2017770 C1 | 8/1994 |
| RU | 2325419 C1 | 2/2008 |
| RU | 2448830 C2 | 10/2011 |
| RU | 2488606 C2 | 1/2012 |
| RU | 2501825 C2 | 5/2012 |
| SU | 431139 A | 6/1974 |
| WO | 8303092 A1 | 3/1983 |
| WO | 8807614 A1 | 10/1988 |
| WO | 9210602 A1 | 6/1992 |
| WO | 9318642 A1 | 9/1993 |
| WO | 9508259 A1 | 3/1995 |
| WO | 9719141 A1 | 5/1997 |
| WO | 9720780 A1 | 6/1997 |
| WO | 9936368 A1 | 7/1999 |
| WO | 9951536 A1 | 10/1999 |
| WO | 0017121 A1 | 3/2000 |
| WO | 0105725 A1 | 1/2001 |
| WO | 0159026 A2 | 8/2001 |
| WO | 0187070 A1 | 11/2001 |
| WO | 0196460 A1 | 12/2001 |
| WO | 0206178 A1 | 1/2002 |
| WO | 2004007615 A1 | 1/2004 |
| WO | 2005068574 A1 | 7/2005 |
| WO | 2006061249 A1 | 6/2006 |
| WO | 2007014236 A2 | 2/2007 |
| WO | 2008005635 A2 | 1/2008 |
| WO | 2008023032 A1 | 2/2008 |
| WO | 2009080696 A2 | 7/2009 |
| WO | 2009080938 A2 | 7/2009 |
| WO | 2010106181 A1 | 9/2010 |
| WO | 2010125163 A1 | 11/2010 |
| WO | 2010132641 A1 | 11/2010 |
| WO | 2011012712 A1 | 2/2011 |
| WO | 2011138458 A1 | 11/2011 |
| WO | 2012013780 A1 | 2/2012 |
| WO | 2012028650 A1 | 3/2012 |
| WO | 2012118939 A1 | 9/2012 |
| WO | 2012166414 A1 | 12/2012 |
| WO | 2014135681 A1 | 9/2014 |
| WO | 2016005481 A1 | 1/2016 |
| WO | 2016102444 A1 | 6/2016 |
| WO | 2017051106 A1 | 3/2017 |

OTHER PUBLICATIONS

J.J. Wilker Nature Chem, Biol. 2011, vol. 7, pp. 579-580.
Sartuqui Javier et al: "Biomimetic fiber mesh scaffolds based on gelatin and hydroxyapatite nano-rods: Designing intrinsic skills to attain bone reparation abilities".COLLOIDS And Surfaces. B. Biointerfaces. Elsevier. Amsterdam. NL. vol. 145. May 9, 2016 (May 9, 2016). pp. 382-391.
Emmett P. Broderick, Damien M. O'Halloran, Yury A. Rochev, Martin Griffin, Russell J. Collighan, Abhay S. Pandit: "Enzymatic stabilization of gelatin-based scaffolds". Journal of Medical Materials Research, vol. 72B, No. 1, Oct. 15, 2004 (Oct. 15, 2004). pp. 37-42.
Irina G Plashchina et al: "Phase behavior of gelatin in the presence of pectin in water-acid medium". Polymer Bulletin, Springer, Berlin, DE. vol. 58, No. 3, Oct. 13, 2006 (Oct. 13, 2006), pp. 587-596.
Bae H J et al: "Effects of transglutaminase-induced cross-linking on properties of fish gelatin-nanoclay composite film", Food Chemistry, Elsevier Ltd. NL, vol. 114, No. 1, May 1, 2009 (May 1, 2009), pp. 180-189.
V. Zitko, J. Rosik: "Reakcia Pektinu so Zelatinou Zlozenie Komplexov Pektinu a Gelatiny", Chemicke Zvesti, vol. XVI, No. 6, Oct. 30, 1961 (Oct. 30, 1961), pp. 474-481.
C. Pena, K. de la Caba, A. Eceiza, R. Ruseckaite, I. Mondragon in Biores. Technol. 2010, 101, pp. 6836-6842.

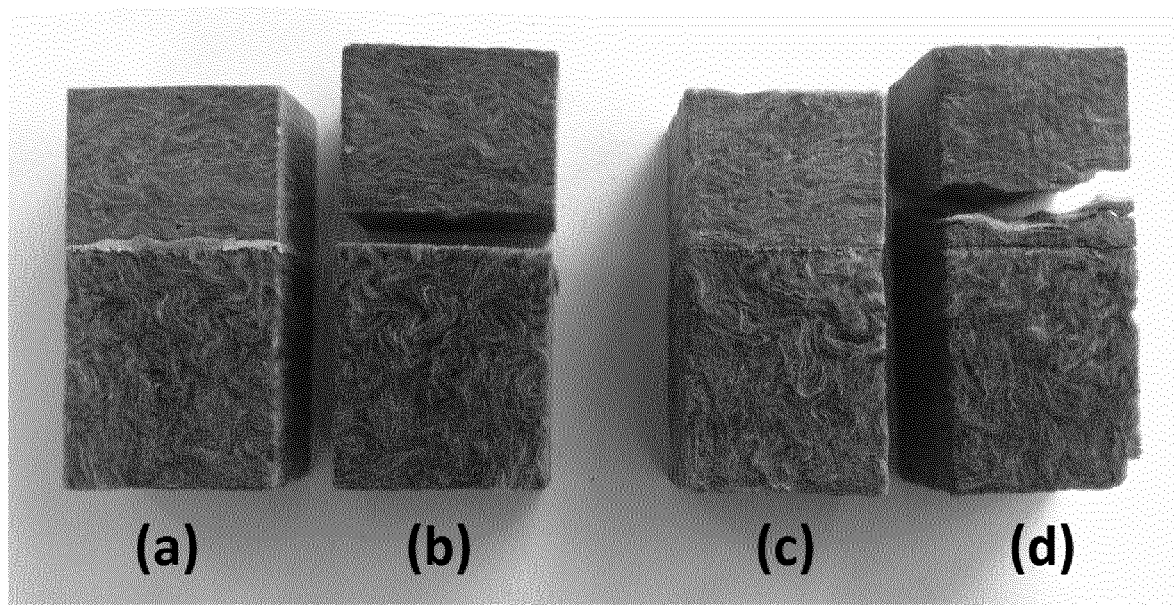

MINERAL WOOL PRODUCT

FIELD OF THE INVENTION

The present invention relates to a method of bonding together the surfaces of two or more elements, whereby at least one of the two or more elements is a mineral wool element, and to a mineral wool product made with said method.

BACKGROUND OF THE INVENTION

Insulating characteristics of ready-made panels depend among other things upon the way in which individual panels are installed and/or bonded together at a construction site. The bigger the number of small panels necessary to form a requested surface, the bigger the number of edges at which panels are in mutual contact. The bigger the number of contact edges between the panels, the bigger the number of thermal bridges will be formed on the insulated surface as a result of inaccurate laying, improper adjustment of individual panels, and also as a result of increased risk of soiling contact surfaces.

Accordingly, there is a need for a method for bonding together the surfaces of two or more such mineral wool panels, or other mineral wool elements.

Further, there is also a need for a method of bonding together the surface of one or more mineral wool elements with one or more element, which is not a mineral wool element.

In the past, phenol-formaldehyde resins which can be economically produced have been used as adhesive compositions for bonding together mineral wool elements.

However, these adhesives suffer from the disadvantage that they contain formaldehyde and they are therefore potentially harmful to handle and require protective measures when handling them on-site.

Non-phenol-formaldehyde binders which can be used as adhesives are sugar based binders, such as for example the compositions disclosed in EP2990494A1, PCT/EP2015/080758, WO2007/014236, WO2011/138458 and WO2009/080938.

However, all these binders, when used as adhesives for bonding together the surfaces of mineral wool elements, suffer from the disadvantage that they require high temperatures for curing which makes it necessary to apply heat over a prolonged time to the elements to be bonded together. This does not only require additional equipment but can also cause a fire hazard, e.g. when bonding together isolation elements for a roof insulation on-site. Further, the high temperature curing of these known adhesives can cause the emission of harmful or irritating fumes which may require protective measures for the handling of this matter.

Another type of adhesive that has been used for gluing together mineral wool elements with each other or with other elements such as glass fleece or metal sheet is a polyurethan based adhesive. This may be a one- or two-component adhesive. Such adhesives have do not necessarily have to be cured at high temperatures. However, these adhesives may also be harmful when handling and are not based on naturally occurring ingredients.

Other adhesives are based on PVA, bitumen, inorganic binders PUR, and/or polyacrylates.

SUMMARY OF THE INVENTION

Accordingly, it was an object of the present invention to provide a method of bonding together the surfaces of two or more elements, whereby at least one of the two or more elements is a mineral wool element, whereby the method uses an adhesive that does not require high temperatures for curing and whereby during the handling, application, and curing of the adhesive exposure to harmful substances is minimized and no protective measures are necessary.

In accordance with a first aspect of the present invention, there is provided a method of bonding together the surfaces of two or more elements, whereby at least one of the two or more elements is a mineral wool element, said elements being bound by a mineral wool binder, the method comprising the steps of:
  providing two or more elements,
  applying an adhesive to one or more of the surfaces to be bonded together before, during or after contacting the surfaces to be bonded together with each other,
  curing the adhesive, wherein the adhesive comprises,
  at least one protein,
  at least one phenol and/or quinone containing compound, and/or at least one enzyme.

In accordance with a second aspect of the present invention, there is provided a product made by the described method.

We find that the use of this particular type of adhesive, especially when it has the preferred features set out, provides particularly durable connections for mineral wool elements.

The present inventors have surprisingly found that it is possible to bond together the surfaces of mineral wool elements with each other or of one or more mineral wool element with another element by using the method described. Since the adhesive used for the method in some embodiments does usually not contain any harmful substances and does usually not set free any harmful substances during the curing, the method can be carried out by any person on-site of use without any protective measures and without a need for specific training for the persons to carry out the method.

BRIEF DESCRIPTION OF THE DRAWING

In the accompanying drawing, FIG. 1 shows photographs of four samples of roof boards bonded with two different adhesives before and after aging and pulling the bonded surfaces apart.

DESCRIPTION OF THE PREFERRED EMBODIMENTS

The method of bonding together the surfaces of two or more elements, whereby at least one of the two or more elements is a mineral wool element, said elements being bound by a mineral wool binder, comprises the steps of:
  providing two or more elements,
  applying an adhesive to one or more of the surfaces to be bonded together before, during or after contacting the surfaces to be bonded together with each other,
  curing the adhesive, wherein the adhesive comprises,
  at least one protein,
  at least one phenol and/or quinone containing compound, and/or at least one enzyme.

In a preferred embodiment, the adhesive is applied to one or more of the surfaces to be bonded together before contacting the surfaces to be bonded together with each other.

The method according to the present invention can both be used for bonding together two or more mineral wool elements, like e.g. isolation panels, and to bond together one or more mineral wool elements with one or more element which is not a mineral wool element.

In one embodiment, the two or more elements to be bonded together are two or more mineral wool elements.

In another embodiment, the two or more elements to be bonded together comprise at least one element, which is not a mineral wool element.

It has surprisingly being found that the adhesive used in the method according to the present invention can not only be used for binding mineral wool elements together but also for binding one or more mineral wool elements to an element, which is not a mineral wool element.

In a preferred embodiment, at least one element, which is not a mineral wool element, is selected from the group consisting of a fleece, a wall, plasterboard, metal, plastic, wood, metal, plastic tubes and/or pipes.

The Mineral Wool Element

Mineral wool elements generally comprise man-made vitreous fibres (MMVF) such as, e.g., glass fibres, ceramic fibres, basalt fibres, slag wool, mineral wool and stone wool (rock wool), which are bonded together by a cured mineral wool binder such as a thermoset polymeric binder material. For use as thermal or acoustical insulation products, bonded mineral fibre mats are generally produced by converting a melt made of suitable raw materials to fibres in conventional manner, for instance by a spinning cup process or by a cascade rotor process. The fibres are blown into a forming chamber and, while airborne and while still hot, are sprayed with a binder solution and randomly deposited as a mat or web onto a travelling conveyor. The fibre mat is then transferred to a curing oven where heated air is blown through the mat to cure the binder and rigidly bond the mineral fibres together.

If desired, the web may be subjected to a shaping process before curing. The bonded mineral fibre element may be cut to a desired format e.g., in the form of a batt. Thus, the mineral wool elements, for instance, have the form of woven and nonwoven fabrics, mats, batts, slabs, sheets, plates, strips, rolls, granulates and other shaped articles which find use for example, as thermal or acoustical insulation materials, vibration damping, construction materials, facade insulation, reinforcing materials for roofing or flooring applications, as filter stock, as horticultural growing media and in other applications.

The Mineral Wool Binder

The mineral wool binder is conventionally phenol-formaldehyde resins which can be economically produced and can be extended with urea prior to use as a binder. However, the existing and proposed legislation directed to the lowering or elimination of formaldehyde emissions have led to the development of formaldehyde-free binders.

One group of non-phenol-formaldehyde binders are the addition/-elimination reaction products of aliphatic and/or aromatic anhydrides with alkanolamines, e.g., as disclosed in WO 99/36368, WO 01/05725, WO 01/96460, WO 02/06178, WO 2004/007615 and WO 2006/061249. These binder compositions are water soluble and exhibit excellent binding properties in terms of curing speed and curing density. WO 2008/023032 discloses urea-modified binders of that type which provide mineral wool products having reduced moisture take-up.

Another group of non-phenol-formaldehyde binders are sugar based binders, such as for example disclosed in EP2990494A1, PCT/EP2015/080758, WO2007/014236, WO2011/138458 and WO2009/080938.

Another group of binders are binders comprising at least one protein, and at least one enzyme.

Another group of binders are binders comprising at least one phenol and/or quinone containing compound, and at least one protein.

The Adhesive for Use in the Method of the Present Invention

In a preferred embodiment, the adhesive comprises at least 70 wt. % protein based on the total adhesive component solids content.

In a further preferred embodiment, the adhesive further comprises at least one additive.

It is preferred that the curing of the adhesive is carried out at temperatures from 5 to 95° C., such as 5 to 80° C., such as 10 to 60° C., such as 20 to 40° C.

In a preferred embodiment, the curing of the adhesive comprises a drying process, in particular by blowing air or gas over the or more elements or by increasing temperature.

The adhesive used for the method according to the present invention comprises protein as one mandatory constituent.

Preferably, the protein component of the adhesive is in form of one or more proteins selected from the group consisting of proteins from animal sources, including collagen, gelatine, hydrolysed gelatine, and protein from milk (casein, whey), eggs; proteins from vegetable sources, including proteins from legumes, cereals, whole grains, nuts, seeds and fruits, like protein from buckwheat, oats, rye, millet, maize (corn), rice, wheat, bulgar, sorghum, amaranth, quinoa, soybeans (soy protein), lentils, kidney beans, white beans, mung beans, chickpeas, cowpeas, lima beans, pigeon peas, lupines, wing beans, almonds, Brazil nuts, cashews, pecans, walnuts, cotton seeds, pumpkin seeds, hemp seeds, sesame seeds, and sunflower seeds; polyphenolic proteins such as mussel foot protein.

Collagen is a very abundant material in living tissue: It is the main component in connective tissue and constitutes 25-35% of the total protein content in mammals. Gelatin is derived from chemical degradation of collagen. Gelatin is water soluble and has a molecular weight of 30.000 to 300.000 g/mol dependent on the grade of hydrolysis. Gelatin is a widely used food product and it is therefore generally accepted that this compound is totally non-toxic and therefore no precautions are to be taken when handling gelatin.

The gelatin can also be further hydrolysed to smaller fragments of down to 3000 g/mol.

In a preferred embodiment, the protein component is gelatin, whereby the gelatin is preferably originating from one or more sources from the group consisting of mammal, bird species, such as from cow, pig, horse, fowl, and/or from scales, skin of fish.

Adhesive Based on Protein Component and Phenol and/or Quinone Containing Compound Component In one embodiment, the present invention is directed to a method of bonding together the surfaces of two or more elements, whereby at least one of the two or more elements is a mineral wool element, said mineral wool element(s) being bound by a mineral wool binder, the method comprising the steps of:
  providing two or more elements,
  applying an adhesive to one or more of the surfaces to be bonded together before, during or after contacting the surfaces to be got bonded together with each other,
  curing the adhesive, wherein the adhesive comprises,
  at least one protein,
  at least one phenol and/or quinone containing compound.

The adhesive according to this embodiment of the present invention comprises a phenol and/or quinone containing compound component, in particular one or more phenolic compound and/or one or more quinone.

Phenolic compounds, or phenolics, are compounds that have one or more hydroxyl group attached directly to an aromatic ring. Polyphenols (or polyhydroxyphenols) are compounds that have more than one phenolic hydroxyl group attached to one or more aromatic rings. Phenolic compounds are characteristic of plants and as a group they are usually found as esters or glycosides rather than as free compounds.

The term phenolics covers a very large and diverse group of chemical compounds. Preferably, the phenol containing compound is a compound according to the scheme based on the number of carbons in the molecule as detailed in by W. Vermerris, R. Nicholson, in *Phenolic Compound Biochemistry*, Springer Netherlands, 2008.

Preferably, the phenol containing compound is in form of one or more components selected from the group consisting of a compound with a $C_6$ structure such as simple phenolics, such as resorcinol, phloroglucinol, such as a compound with a $C_6$-$C_1$ structure such as hydroxybenzoic acids, such as p-hydroxybenzoic acid, gallic acid, protocathechuic acid, salicylic acid, vanillic acid, such as hydroxybenzoic aldehydes, such as vanillin, such as a compound with a $C_6$-$C_2$ structure such as hydroxyacetophenones, such as 2-hydroxyacetophenone, such as hydroxy-phenylacetic acids, such as 2-hydroxyphenyl acetic acid, such as a compound with a $C_6$-$C_3$ structure such as cinnamic acids, such as p-coumaric acid, caffeic acid, ferulic acid, 5-hydroxyferulic acid, sinapic acid, such as cinnamic acid esters, such as chlorogenic acid, sinapoyl malate, sinapoyl choline, such as cinnamyl aldehydes, such as cinnamyl alcohols, such as coumarins, such as umbelliferone, 4-methyl umbelliferone, such as isocoumarins, such as bergenin, such as chromones, such as a compound with a $C_{15}$ structure such as flavonoids, such as flavanone, isoflavones, isoflavanones, neoflavanoids, such as chalcones, such as butein, such as dihydrochalcones, such as phloridzin, such as aurones, such as flavanones, such as naringenin, such as flavanonols, such as taxifolin, such as flavans, such as leucoanthocyanidins, such as leucocyanidin, leucodelphinidin, such as flavan-3-ols, such as catechin, gallocatechin, such as flavones, such as kaemferol, quercetin, myricetin, such as anthocyanidins, such as pelargonidin, cyanidin, peonidin, delphinidin, petunidin, malvidin, such as deoxyanthocyanidines, such as apigeninidin, luteolinidin, 7-methoxyapigeninidin, 5-methoxyluteolinidin, such as anthocyanins, such as petanin, such as a compound with a $C_{30}$ structure such as biflavonyls, such as ginkgetin, such as a compound with a $C_6$-$C_1$-$C_6$ structure such as benzophenones, such as xanthones, such as a compound with a $C_6$-$C_2$-$C_6$ structure such as stilbenes, such as resveratrol, pinosylvin, such as a compound with a $C_6/C_{10}/C_{14}$ structure such as benzoquinones, such as naphthaquinones, such as juglone, such as anthraquinones, such as emodin, such as a compound with a $C_{18}$ structure such as betacyanins, such as betanidin, such as polyphenols and/or polyhydroxyphenols, such as lignans, neolignans (dimers or oligomers from coupling of monolignols such as p-coumaryl alcohol, coniferyl alcohol and sinapyl alcohol), such as pinoresinol, sesamin, plicatic acid, such as lignins (synthesized primarily from the monolignol precursors p-coumaryl alcohol, coniferyl alcohol and sinapyl alcohol), such as tannins, such as condensed tannins (proanthocyanidins), such as procyanidin $B_2$, such as hydrolysable tannins, such as gallotannins, such as ellagitannins, such as complex tannins, such as acutissimin A, such as tannic acid, such as phlobabenes.

In a preferred embodiment, the phenol containing compound is selected from the group consisting of simple phenolics, phenol containing compounds with a more complex structure than a $C_6$ structure, such as oligomers of simple phenolics, polyphenols, and/or polyhydroxyphenols.

Quinones are oxidized derivatives of aromatic compounds and are often readily made from reactive aromatic compounds with electron-donating substituents such as phenolics. Quinones useful for the present invention include benzoquinones, napthoquinone, anthraquinone and lawsone.

The phenol and/or quinone containing compounds according to the present invention can also be synthetic or semisynthetic molecules or constructs that contain phenols, polyphenols and/or quinones. An example for such a construct is a protein, peptide, peptoids (such as linear and/or cyclic oligomers and/or polymers of N-substituted glycines, N-substituted β-alanines), or arylopeptoids (such as linear and/or cyclic oligomers and/or polymers of N-substituted aminomethyl benzamides) modified with phenol and/or quinone containing side chains. A dendrimer decorated with phenol and/or quinone containing side chains is another example.

Tannins comprise a group of compounds with a wide diversity in structure that share their ability to bind and precipitate proteins. Tannins are abundant in many different plant species, in particular oak, chestnut, staghorn sumac and fringe cups. Tannins can be present in the leaves, bark and fruits. Tannins can be classified into three groups: condensed tannins, hydrolysable tannins and complex tannins. Condensed tannins, or proanthocyanidins, are oligomeric or polymeric flavonoids consisting of flavan-3-ol (catechin) units. Gallotannins are hydrolysable tannins with a polyol core substituted with 10-12 gallic acid residues. The most commonly found polyol in gallotannins is D-glucose although some gallotannins contain catechin and triterpenoid units as the core polyol. Ellagitanins are hydrolysable tannins that differ from gallotannins in that they contain additional C—C bonds between adjacent galloyl moieties. Complex tannins are defined as tannins in which a catechin unit is bound glycosidically to either a gallotannin or an ellagitannin unit.

The inventors have surprisingly found that a wide range of such phenol and/or quinone containing compounds can be used to crosslink proteins which allows a binder composition to be formed. Often, these phenol and/or quinone containing compounds are obtained from vegetable tissues and are therefore a renewable material. In some embodiments, the compounds are also non-toxic and noncorrosive. As a further advantage, these compounds are antimicrobial and therefore impart their antimicrobial properties to the mineral wool product bound by such a binder.

In a preferred embodiment, the phenol and/or quinone containing compound is selected from one or more components from the group consisting of tannic acid, ellagitannins and gallotannins, tannin originating from one or more of oak, chestnut, staghorn sumac and fringe cups.

In a particular preferred embodiment, the phenol and/or quinone containing compound component is a tannin and/or tannic acid, and the protein component is gelatin, in particular gelatin from porcine skin, in particular of medium gel strength, or low gel strength.

Without wanting to be bound to any particular theory, the present inventors believe that the reaction between the phenol and/or quinone containing compound and the protein at least partly relies on a oxidation of phenols to quinones followed by nucleophilic attack of amine and/or thiol groups from the protein which leads to a crosslinking of the proteins by the phenol and/or quinone containing compounds.

In a preferred embodiment, the content of the phenol and/or quinone containing compound in the adhesive according to the present invention is from 1 to 70 wt. %, such as 2 to 60 wt. %, such as 3 to 50 wt. %, such as 4 to 40 wt. %, such as 5 to 35 wt. %, based on dry protein basis.

In an alternative preferred embodiment, the mass ratio of (lysine+cystein) in the protein to (phenol+quinone) in the phenol and/or quinone containing compound is 1:5.78-1:0.08, such as 1:2.89-1:0.09, such as 1:1.93-1:0.12, such as 1:1.45-1:0.15, such as 1:1.16-1:0.17.

The present inventors have found that the curing of the adhesive is accelerated under alkaline conditions. Therefore, in one embodiment, the adhesive for mineral fibres comprises a pH-adjuster, preferably in form of a base, such as organic base, such as amine or salts thereof, inorganic bases, such as metal hydroxide, such as KOH or NaOH, ammonia or salts thereof.

In a particular preferred embodiment, the pH adjuster is an alkaline metal hydroxide, in particular NaOH.

In a preferred embodiment, the adhesive according to the present invention has a pH of 7 to 10, such as 7.5 to 9.5, such as 8 to 9.

In one embodiment, the protein comprises polyphenolic proteins.

These proteins contain a high level of a post-translationally modified-oxidized-form of tyrosine, L-3,4-dihydroxyphenylalanine (levodopa, L-DOPA). See also J. J. Wilker Nature Chem. Biol. 2011, 7, 579-580 for a reference to these proteins.

In a preferred embodiment, the adhesive according to the present invention contains additives.

Additives may be components such as one or more reactive or nonreactive silicones and may be added to the adhesive. Preferably, the one or more reactive or nonreactive silicone is selected from the group consisting of silicone constituted of a main chain composed of organosiloxane residues, especially diphenylsiloxane residues, alkylsiloxane residues, preferably dimethylsiloxane residues, bearing at least one hydroxyl, acyl, carboxyl or anhydride, amine, epoxy or vinyl functional group capable of reacting with at least one of the constituents of the adhesive and is preferably present in an amount of 0.1-15 weight-%, preferably from 0.1-10 weight-%, more preferably 0.3-8 weight-%, based on the total adhesive mass.

In one embodiment, an emulsified hydrocarbon oil may be added to the adhesive.

As already described above, many polyphenols have antimicrobial properties and therefore impart antimicrobial characteristic to the adhesive. Nevertheless, in one embodiment, an anti-fouling agent may be added to the adhesives.

In one embodiment, an anti-swelling agent may be added to the adhesive, such as tannic acid and/or tannins.

In one embodiment, the adhesive according to the present invention contains additives in form of amine linkers and/or thiol/thiolate linkers. These additives in form of amine linkers and/or thiol/thiolate linkers are particular useful when the crosslinking reaction of the adhesive proceeds via the quinone-amine and/or quinone-thiol pathway.

In one embodiment, the adhesives according to the present invention comprise an additive containing metal ions, such as iron ions.

Polyphenolic proteins such as the mussel adhesive protein discussed above relies on 3,4-dihydroxyphenyl moieties to enhance the surface adhesion. This is achieved in combination with the secretion of selected types of cations such as iron ions. In one embodiment, the adhesive could be said to mimic the polyphenolic protein and therefore the addition of various cations could improve the adhesive characteristics.

Such advantageous ions can also be released from the mineral fibre surface when they come into contact with the aqueous adhesive.

In one embodiment, the mineral wool elements bonded by the method according to the present invention comprise rock wool. Without being bound by theory, it is believed that leaching of certain ions from the vitreous fibres may assist the adhesive strength. The mechanism may be analogue to the mechanism for which mussel adhesive protein obtains a surface adhesion. This is achieved in combination with the secretion of selected types of cations such as iron ions.

In one embodiment, the adhesives according to the present invention contain further additives in form of additives selected from the group consisting of PEGtype reagents, silanes, and hydroxylapatites.

Oxidising agents as additives can serve to increase the oxidising rate of the polyphenols. One example is the enzyme tyrosinase which oxidizes phenols to hydroxyphenols/quinones and therefore accelerates the adhesive forming reaction. In another embodiment, the oxidising agent is oxygen, which is supplied to the adhesive.

In one embodiment, the curing is performed in oxygen-enriched surroundings.

Adhesive Based on Protein Component and Enzyme Component

In an alternative embodiment, the adhesive used in the method according to the present invention is based on a protein component and an enzyme component.

According to this embodiment, the invention is directed to a method of bonding together the surfaces of two or more elements, whereby at least one of the two or more elements is a mineral wool element, said mineral wool element(s) being bound by a mineral wool binder, the method comprising the steps of:
  providing two or more elements,
  applying an adhesive to one or more of the surfaces to be bonded together before, during or after contacting the surfaces to be bonded together with each other,
  curing the adhesive, wherein the adhesive comprises,
  at least one protein,
  and/or at least one enzyme.

In a preferred embodiment, the enzyme component of the adhesive is selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

The enzymes can be both of natural sources and of recombinant sources.

In a particular preferred embodiment, the protein component is gelatine, in particular gelatine from porcine skin, in particular of medium gels strength, and the enzyme component is transglutaminase (EC 2.3.2.13).

The present inventors have found that for some embodiments the method according to the present invention is best carried out when the adhesive based on the protein component and enzyme component is applied under acidic conditions.

Therefore, in a preferred embodiment, the adhesive comprises a pH adjuster, in particular in form of a pH buffer.

In a preferred embodiment, the adhesive in its uncured state has a pH value of less than 8, such as less than 7, such as less than 6.

Other additives may be components such as one or more reactive or nonreactive silicones and may be added to the adhesive. Preferably, the one or more reactive or nonreactive silicone is selected from the group consisting of silicone constituted of a main chain composed of organosiloxane residues, especially diphenylsiloxane residues, alkylsiloxane residues, preferably dimethylsiloxane residues, bearing at least one hydroxyl, acyl, carboxyl or anhydride, amine, epoxy or vinyl functional group capable of reacting with at least one of the constituents of the adhesive and is preferably present in an amount of 0.1-15 weight-%, preferably from 0.1-10 weight-%, more preferably 0.3-8 weight-%, based on the total adhesive mass.

In one embodiment, a silane may be added to the adhesive.

In one embodiment, an emulsified hydrocarbon oil may be added to the adhesive.

In one embodiment, an anti-fouling agent may be added to the adhesive.

In one embodiment, an anti-swelling agent may be added to the adhesive, such as tannic acid and/or tannins.

Further additives may be additives containing calcium ions (which stabilises the transglutaminase enzyme), and antioxidants.

In one embodiment, the adhesive according to the present invention contains additives in form of linkers containing acyl groups and/or amine groups and/or thiol groups. These linkers can strengthen and/or modify the network of the cured adhesive.

In one embodiment, the adhesives according to the present invention contain further additives in form of additives selected from the group consisting of PEGtype reagents, silanes, and hydroxylapatites.

The Adhesive Process

In one embodiment, after application of the adhesive the elements are subjected to pressure during bonding and preferably the total time for application of the adhesive and subjection to pressure is not more than 120 seconds, such as 60 seconds, such as 30 seconds, such as 20 seconds.

In one embodiment, the panels can be moved along stationary nozzles or stationary panels can be sprayed with the use of movable nozzles or applied with rollers. Spraying time and adhesive bonding time is 120 seconds maximum. Panels sprayed with the adhesive are pressed together.

In one embodiment, the adhesive can be applied to just one of the surfaces to be bonded but it may be applied to both.

In one embodiment, the protein component of the adhesive can be applied to a first surface to be bonded and the phenol and/or quinone containing compound and/or at least one enzyme can be applied to a second surface to be bonded and then the first and second surfaces are contacted with each other.

It is advantageous to achieve a balanced penetration of the adhesive into deeper layers of the element; such a connection would be more durable than a connection made by another method. Generally the adhesive does not penetrate more than 2 mm into the element.

In one embodiment, the amount of cured adhesive is 10-1000 $g/m^2$ surface, such as 50-500 $g/m^2$ surface, such as 100-400 $g/m^2$ surface.

In one embodiment, the adhesive is applied by means of a spraying, rolling, brushing, curtain painting, a sponge or a soft sponge roll.

The Product

The present invention is also directed to a product made by the method described above, such as a product where at least one of the elements is a mineral wool product.

In a preferred embodiment, the product comprises at least one element being a mineral wool product, wherein the density of the mineral wool product is in the range of 10-1200 $kg/m^3$, such as 30-800 $kg/m^3$, such as 40-600 $kg/m^3$, such as 50-250 $kg/m^3$, such as 60-200 $kg/m^3$.

In a preferred embodiment, the mineral wool product according to the present invention is an insulation product, in particular having a density of 10 to 200 $kg/m^3$.

In one embodiment, the product produced by the method described above is a product, wherein the mineral wool product comprises a fleece which is bonded to a mineral wool element with the method described above.

A Mineral Wool Product

In one embodiment, two or three (and in some cases more) elements can be bonded together to form an insulation panel. The elements are bonded together at their largest surfaces. For example, the bottom surface of the first element is bonded to the top surface of the second element and the bottom surface of the second element is bonded to the top surface of the third element. Alternatively, in another embodiment, the major surfaces may be bonded together irrespective of being top- or bottom-surfaces.

The insulation panels provided are useful for insulating various surfaces, including roofs, external walls of buildings and ceilings. They may be used as sound, thermal or fire insulation.

In one embodiment, a flat roof structure is insulated with mineral wool insulation elements whereby the elements are laid out on the flat roof in two layers, a top and bottom layer and elements from the top layer are bonded to elements from the bottom layer with the adhesive.

In one embodiment, an outer or inner wall is insulated with mineral wool insulation elements whereby the elements are placed on the outer or inner wall in two layers, a layer facing the wall and an outwards facing layer and elements from the layer facing the wall are bonded to outwards facing layers with the adhesive. The outer wall insulated in this way may form part of an ETICS (External Thermal Insulation Composite System).

A Granulate Product

In one embodiment, the mineral wool product is a product based on a granulate product. A granulate product is conventionally made by producing a cured mineral wool web and then subjecting the web to a granulation process so that granules are formed. The granules typically have a size of 1-5 cm and the binder content amounts to an LOI-value typically around 1%. The granules are packaged in a compressed state and the package is then opened at the building site to apply the granulate product with a blowing equipment to e.g. a horizontal attic, in between walls or another structure.

The adhesive is supplied before or during the application of the granulate product, thereby adhering the granules being mineral wool elements to each other. The granules and the adhesive provides a granulate mineral wool product which has improved properties such as being prone to less dusting and providing a more rigid structure which is less prone to collapsing under its own weight.

In an alternative embodiment the granules and the adhesive provides a granulate mineral wool product which adheres to a building structure such as a wall or a ceiling so that the mineral wool product fully or partly coat the building structure.

A Sandwich Panel Product

In one embodiment, the mineral wool product is a so-called sandwich panel core. A sandwich panel core may be made by the general method where a cured mineral wool web is cut longitudinally into elements being lamellae and the lamellae thus formed are turned 90° about their longitudinal axis where after the lamellae thus oriented are bonded together with the adhesive to form a web-like product which is then cut into desired lengths to form board elements. Due to the turning of the lamellae the fibres of the finished boards will predominantly be oriented in a plane perpendicular to the surfaces of the boards and as a result thereof boards having a considerable stiffness and strength perpendicularly to the surfaces of the boards are obtained.

The sandwich panel core is provided with metal sheets on major surfaces of the panel to provide a sandwich panel product, such as by adhesion with the adhesive.

A Mineral Wool Product Comprising a Fleece

A mineral wool product or element may be applied with an adhesive to one or both of the surfaces such as a major surface, the fleece is then contacted with said surface and the adhesive is cured. Alternatively or in addition, the fleece may be applied with the adhesive before contacting.

Other items than fleeces may be adhered to mineral wool products or elements with the method steps according to the invention.

Such other items may be made of a wall, plasterboard, metal, plastic.

EXAMPLES

In the following examples, several products which fall under the definition of the present invention were prepared and compared to products according to the prior art.

Products Made with Binders According to the Prior Art

Two stone wool roof boards with densities of approximately 150 kg/m$^3$ were made with two different binders (binder A and binder B, see mixing examples below) according to the prior art.

The following properties were determined for the binders according the prior art.

Reagents

50% aq. hypophosphorous acid and 28% aq. ammonia were supplied by Sigma Aldrich. 75.1% aq. glucose syrup with a DE-value of 95 to less than 100 (C*sweet D 02767 ex Cargill) was supplied by Cargill. Silane (Momentive VS-142) was supplied by Momentive and was calculated as 100% for simplicity. All other components were supplied in high purity by Sigma-Aldrich and were assumed anhydrous for simplicity.

Binder Solids—Definition and Procedure

The content of binder after curing is termed "binder solids".

Disc-shaped stone wool samples (diameter: 5 cm; height 1 cm) were cut out of stone wool and heat-treated at 580° C. for at least 30 minutes to remove all organics. The solids of the binder mixture (see below for mixing examples) were measured by distributing a sample of the binder mixture (approx. 2 g) onto a heat treated stone wool disc in a tin foil container. The weight of the tin foil container containing the stone wool disc was weighed before and directly after addition of the binder mixture. Two such binder mixture loaded stone wool discs in tin foil containers were produced and they were then heated at 200° C. for 1 hour. After cooling and storing at room temperature for 10 minutes, the samples were weighed and the binder solids was calculated as an average of the two results. A binder with the desired binder solids could then be produced by diluting with the required amount of water and 10% aq. silane (Momentive VS-142).

Binder Example, Binder A (Phenol-Formaldehyde Resin Modified with Urea, a PUF-Resol)

A phenol-formaldehyde resin is prepared by reacting 37% aq. formaldehyde (606 g) and phenol (189 g) in the presence of 46% aq. potassium hydroxide (25.5 g) at a reaction temperature of 84° C. preceded by a heating rate of approximately 1° C. per minute. The reaction is continued at 84° C. until the acid tolerance of the resin is 4 and most of the phenol is converted. Urea (241 g) is then added and the mixture is cooled.

The acid tolerance (AT) expresses the number of times a given volume of a binder can be diluted with acid without the mixture becoming cloudy (the binder precipitates). Sulfuric acid is used to determine the stop criterion in a binder production and an acid tolerance lower than 4 indicates the end of the binder reaction. To measure the AT, a titrant is produced from diluting 2.5 ml conc. sulfuric acid (>99%) with 1 L ion exchanged water. 5 mL of the binder to be investigated is then titrated at room temperature with this titrant while keeping the binder in motion by manually shaking it; if preferred, use a magnetic stirrer and a magnetic stick. Titration is continued until a slight cloud appears in the binder, which does not disappear when the binder is shaken.

The acid tolerance (AT) is calculated by dividing the amount of acid used for the titration (mL) with the amount of sample (mL):

$$AT = (\text{Used titration volume (mL)})/(\text{Sample volume (mL)})$$

Using the urea-modified phenol-formaldehyde resin obtained, a binder is made by addition of 25% aq. ammonia (90 mL) and ammonium sulfate (13.2 g) followed by water (1.30 kg). The binder solids were then measured as described above and the mixture was diluted with the required amount of water and silane (0.5% silane of binder solids, Momentive VS-142).

Binder Example, Binder B

A mixture of L-ascorbic acid (1.50 g, 8.52 mmol) and 75.1% aq. glucose syrup (18.0 g; thus efficiently 13.5 g glucose syrup) in water (30.5 g) was stirred at room temperature until a clear solution was obtained. 50% aq. hypophosphorous acid (0.60 g; thus efficiently 0.30 g, 4.55 mmol hypophosphorous acid) and urea (0.75 g) were then added. 28% aq. ammonia (0.99 g; thus efficiently 0.28 g, 16.3 mmol ammonia) was then added dropwise until pH=6.9. The binder solids were then measured as described above (21.5%) and the mixture was diluted with the required amount of water and silane (0.5% silane of binder solids, Momentive VS-142). The final binder mixture had pH=7.0.

Adhesives According to the Present Invention

The following properties were determined for the adhesives according the present invention.

Reagents

Medium gel strength gelatin from porcine skin (170-195 g Bloom), tannic acid, sodium hydroxide and potassium hydroxide were obtained from Sigma-Aldrich. For simplicity, these reagents were considered completely pure and anhydrous.

Adhesive Component Solids Content—Definition

The content of each of the components in a given adhesive solution before curing is based on the anhydrous mass of the components. The following formula can be used:

$$\text{adhesive component solids content}(\%) = $$
$$\frac{\text{adhesive component A solids}(g) + }{\text{adhesive component B solids}(g) + \ldots} \times 100\%$$
$$\frac{}{\text{total weight of mixture}(g)}$$

Adhesive Example, Binder 1

Gelatin from porcine skin, medium gel strength (10.0 g) was swelled in water (56.7 g) for 30 min at room temperature. The mixture was then placed in a water bath at 50° C. and stirred a few minutes until a clear solution was obtained (pH 5.1). 1M NaOH (3.10 g) was then added (pH 8.8) and the resulting solution was stirred for 30 minutes further at 50° C. before being used in the subsequent experiments. This adhesive mix had an adhesive component solids content of 14.5%.

Adhesive Example, Adhesive 2

To 1M NaOH (12.0 g) at room temperature was added tannic acid (2.0 g). The resulting mixture was stirred for 15 minutes after which time a brown-greenish solution was obtained.

Gelatin from porcine skin, medium gel strength (10.0 g) was swelled in water (56.7 g) for 30 min at room temperature. The mixture was then placed in a water bath at 50° C. and stirred a few minutes until a clear solution was obtained (pH 4.9). 1M NaOH (3.00 g) was then added (pH 8.9) followed by tannic acid in aq. NaOH (7.0 g, produced as above). The mixture was stirred vigorously for 30 minutes at 50° C. and resulting brown mixture (pH 8.7) was then used in the subsequent experiments. This adhesive mix had an adhesive component solids content of 14.8%.

Examples According to the Present Invention

Samples of 8 cm×5 cm×3 cm (length, width, height) or 8 cm×5 cm×5 cm (length, width, height) were cut from the stone wool roof boards produced with binder A and B.
Bonding and Testing of Samples For each bonding test, one roof board sample made with binder A and one roof board sample made with binder B was placed on a plain surface with one of the 8 cm×5 cm faces up. A sample of adhesive 1 or 2 (2.5 g, prepared as described above) was then transferred to the top face of each of the two roof board samples. The adhesive mixture was spread evenly out over the surfaces using a plastic spatula. The adhesive mixture would penetrate 1-2 mm into the surfaces. One of the two roof board samples was then placed on top of the other so that the two faces where adhesive 1 or 2 had been applied came into contact with each other. A weight of approx. 200 g was placed on top of the connected roof board samples and the agglomerate was left at room temperature for 2-3 days. The bonded samples were then cut into two halves so that one half of the bonded sample could be submitted to ageing tests.

Two such bonding tests were made using adhesive 1 and two such bonding tests were made using adhesive 2.

The samples selected for ageing were submerged into a water bath at 80° C. for 3 h.

After drying for approximately a week at room temperature, selected samples were pulled apart in the direction perpendicular to the newly bonded surfaces.

Samples made with adhesive 1 that had been subjected to ageing treatment would break in the connecting area where adhesive 1 had been applied as the adhesive had dissolved during ageing treatment (see FIG. 1, left). Samples made with adhesive 2 that had been subjected to ageing treatment would instead break in stone wool layers that had not come into contact with adhesive 2 (see FIG. 1, right).

FIG. 1 shows Bonded samples of roof boards made with binder A (top parts) and binder B (bottom parts). (a) and (b): bonded using adhesive 1; (b) has been submitted to ageing conditions followed by pulling perpendicular to the bonded surfaces. (c) and (d): bonded using adhesive 2; (d) has been submitted to ageing conditions followed by pulling perpendicular to the bonded surfaces.

The invention claimed is:

1. A method of bonding together surfaces of two or more elements at least one of which is a mineral wool element which comprises man-made vitreous fibers bonded together by a cured mineral wool binder, wherein the method comprises providing the two or more elements, applying an adhesive to one or more surfaces of the two or more elements to be bonded together, followed by contacting the surfaces to be bonded together with each other, and curing the adhesive to thereby bond the two or more surfaces together, the adhesive comprising (i) at least one protein, and (ii) at least one phenol and/or quinone containing compound, the at least one protein comprising lysine and/or cysteine and a mass ratio of lysine plus cysteine in the at least one protein to phenol plus quinone in the at least one phenol and/or quinone containing compound present in the adhesive being from 1:5.78 to 1:0.08.

2. The method of claim 1, wherein the two or more elements comprise two or more mineral wool elements.

3. The method of claim 1, wherein the two or more elements comprise at least one element which is not a mineral wool element.

4. The method of claim 1, wherein the curing of the adhesive is carried out at a temperature of from 5° C. to 95° C.

5. The method of claim 1, wherein the at least one protein is selected from one or more of collagen, gelatin, hydrolyzed gelatin, and protein from milk, eggs; proteins from legumes, cereals, whole grains, nuts, seeds and fruits, protein from buckwheat, oats, rye, millet, maize, rice, wheat, bulgar, sorghum, amaranth, quinoa, soybeans, lentils, kidney beans, white beans, mung beans, chickpeas, cowpeas, lima beans, pigeon peas, lupines, wing beans, almonds, Brazil nuts, cashews, pecans, walnuts, cotton seeds, pumpkin seeds, hemp seeds, sesame seeds, and sunflower seeds; and mussel foot protein.

6. The method of claim 5, wherein the collagen or gelatin originates from one or more of mammal, bird species and/or from scales, skin of fish.

7. The method of claim 1, wherein the at least one phenol and/or quinone containing compound comprises one or more of hydroxybenzoic acids, hydroxybenzoic aldehydes, hydroxyacetophenones, hydroxy-phenylacetic acids, cinnamic acids, cinnamic acid esters, cinnamyl aldehydes, cinnamyl alcohols, coumarins, iso-coumarins, chromones, flavonoids, chalcones, dihydrochalcones, aurones, flavanones, flavanonols, flavans, leucoanthocyanidins, flavan-3-ols, flavones, anthocyanidins, deoxyanthocyanidines, anthocyanins, biflavonyls, benzophenones, xanthones, stilbenes, benzoquinones, naphthoquinones, anthraquinones, betacyanins, polyphenols and/or polyhydroxyphenols, lignans, neolignans, lignins synthesized primarily from monolignol precursors p-coumaryl alcohol, coniferyl alcohol and sinapyl alcohol, tannins, phlobabenes, benzoquinones, naphthoquinones, anthraquinones, lawsone.

8. The method of claim 7, wherein the tannins are selected from one or more of tannic acid, condensed tannins, hydrolyzable tannins, gallotannins, ellagitannins, complex tannins, and/or tannin originating from one or more of oak, chestnut, staghorn sumac, and fringe cups.

9. The method of claim 1, wherein the at least one phenol and/or quinone containing compound comprises one or more synthetic or semisynthetic molecules that contain phenols, polyphenols and/or quinones.

10. The method of claim 1, wherein the at least one phenol and/or quinone containing compound comprises one or more proteins, peptides, peptoids and/or arylopeptoids which are modified with phenol and/or quinone containing side chains, and dendrimers which are decorated with phenol and/or quinone containing side chains.

11. The method of claim 8, wherein tannin is present in a concentration of from 1 to 70 wt. %, based on dry protein.

12. The method of claim 1, wherein the adhesive further comprises one or more additives selected from oxidants, metal ions, pH-adjusters.

13. The method of claim 1, wherein the adhesive has a pH value of from 7 to 10.

14. The method of claim 1, wherein the adhesive comprises at least one additive selected from linkers containing acyl groups and/or amine groups and/or thiol groups.

15. The method of claim 1, wherein at least one mineral wool element is present in the form of a woven or nonwoven fabric, a mat, a batt, a slab, a sheet, a plate, a strip or a roll.

16. The method of claim 1, wherein at least one mineral wool element is suitable for use as thermal or acoustical insulation material.

17. The method of claim 1, wherein at least one mineral wool element is suitable for use as vibration damping material, construction material, façade insulation, reinforcing material for roofing or flooring applications, filter stock and/or horticultural growing media.

18. The method of claim 1, wherein the mineral wool binder of the mineral wool element is a non-phenol-formaldehyde binder.

* * * * *